United States Patent
Mothilal et al.

(10) Patent No.: US 9,204,842 B2
(45) Date of Patent: Dec. 8, 2015

(54) MEDICAL DEVICE FIXATION ATTACHMENT MECHANISM

(75) Inventors: Kamal Deep Mothilal, Plymouth, MN (US); George Patras, Greenfield, MN (US); Albert H. Dunfee, Byfield, MA (US)

(73) Assignee: Medtronic, Inc., Minneapolis, MN (US)

( * ) Notice: Subject to any disclaimer, the term of this patent is extended or adjusted under 35 U.S.C. 154(b) by 1100 days.

(21) Appl. No.: 13/050,417

(22) Filed: Mar. 17, 2011

(65) Prior Publication Data
US 2012/0109002 A1 May 3, 2012

Related U.S. Application Data

(60) Provisional application No. 61/408,073, filed on Oct. 29, 2010.

(51) Int. Cl.
*A61B 5/00* (2006.01)
*A61B 5/0215* (2006.01)
*A61N 1/05* (2006.01)
*A61N 1/372* (2006.01)

(52) U.S. Cl.
CPC ............. *A61B 5/6876* (2013.01); *A61B 5/0215* (2013.01); *A61B 5/6882* (2013.01); *A61N 1/057* (2013.01); *A61N 1/37205* (2013.01)

(58) Field of Classification Search
CPC .......... A61B 1/00; A61B 5/00; A61B 5/6876
USPC ....... 600/585, 549; 606/60; 623/16; 128/899; 433/201.1
See application file for complete search history.

(56) References Cited

U.S. PATENT DOCUMENTS

| | | | |
|---|---|---|---|
| 5,988,171 A | 11/1999 | Sohn et al. | |
| 6,183,255 B1 * | 2/2001 | Oshida | 433/201.1 |
| 6,183,478 B1 | 2/2001 | Konieczynski | |
| 6,221,024 B1 | 4/2001 | Miesel | |
| 6,249,709 B1 | 6/2001 | Conger et al. | |
| 6,986,784 B1 | 1/2006 | Weiser et al. | |
| 7,166,127 B2 | 1/2007 | Spence et al. | |
| 7,214,230 B2 | 5/2007 | Brock et al. | |
| 7,431,726 B2 * | 10/2008 | Spence et al. | 606/151 |
| 7,463,934 B2 | 12/2008 | Tronnes et al. | |
| 7,546,165 B2 | 6/2009 | Zarembo et al. | |
| 7,899,553 B2 | 3/2011 | Barker | |
| 8,574,149 B2 * | 11/2013 | Evans et al. | 600/37 |
| 2002/0173731 A1 * | 11/2002 | Martin et al. | 600/549 |
| 2003/0066538 A1 * | 4/2003 | Martinelli et al. | 128/899 |
| 2006/0241736 A1 * | 10/2006 | Haldeman | 607/126 |
| 2008/0255555 A1 * | 10/2008 | Justis et al. | 606/60 |
| 2009/0319015 A1 * | 12/2009 | Horn-Wyffels | 607/131 |
| 2011/0029057 A1 | 2/2011 | Flach et al. | |
| 2012/0271134 A1 * | 10/2012 | Allan et al. | 600/373 |

OTHER PUBLICATIONS

MatWeb, TIMET TIMETAL® 6-4 ELI Titanium Alloy (Ti-6AI-4V ELI; ASTM Grade 23) (Annealed; <1.75 in Rod or Thickness; Per ASTM F136), 2014.*
International Search Report and Written Opinion of international application No. PCT/US2011/034204, dated Sep. 7, 2011, 10 pp.
International Preliminary Report on Patentability from International Application No. PCT/US2011/034204, dated May 10, 2013, 7 pp.

* cited by examiner

Primary Examiner — Brian Szmal

(57) ABSTRACT

A fixation member configured to anchor an implantable medical device within a patient is attached to an implantable medical device by introducing at least a portion of the fixation member in a tube mechanically connected to the medical device, and plastically deforming the tube in order to pinch the fixation member within a hollow space of the tube.

19 Claims, 8 Drawing Sheets

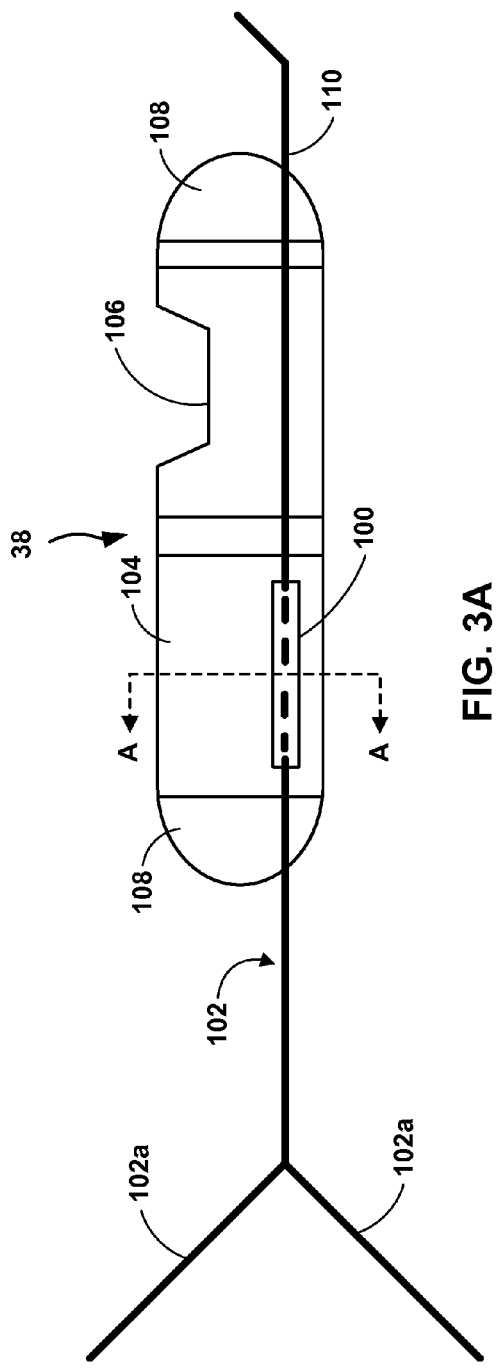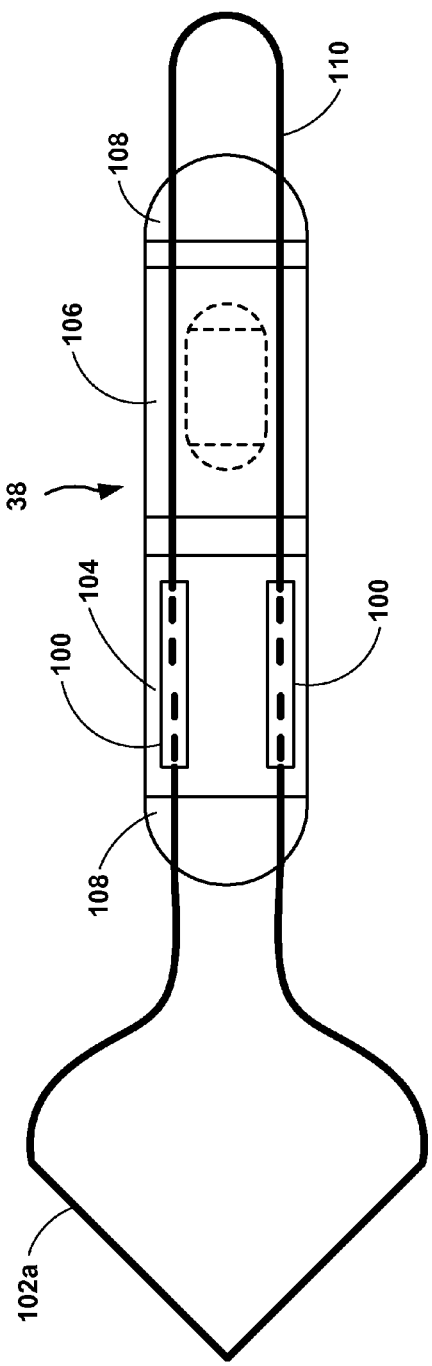
FIG. 3A
FIG. 3B

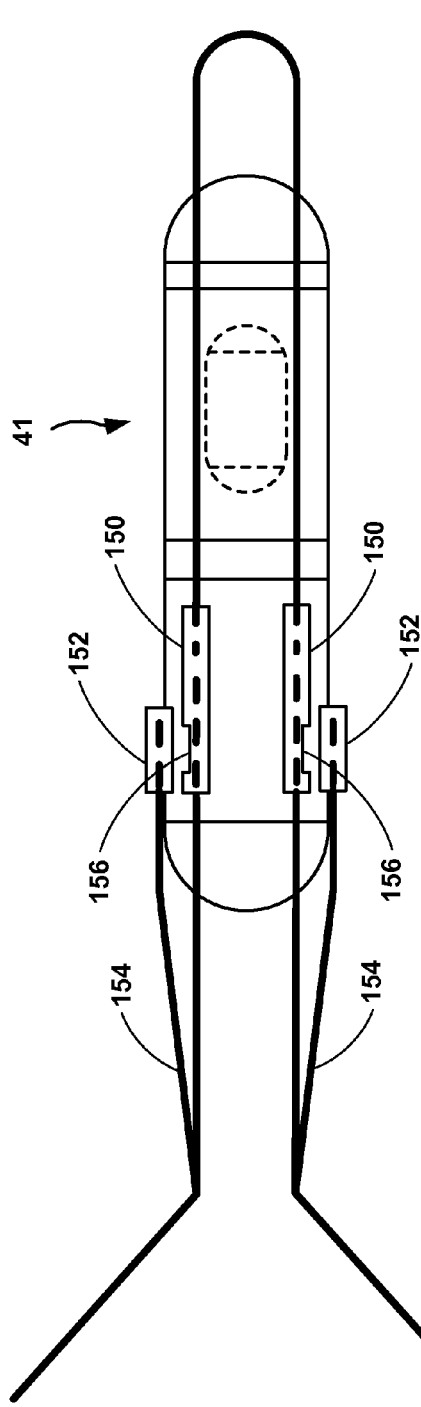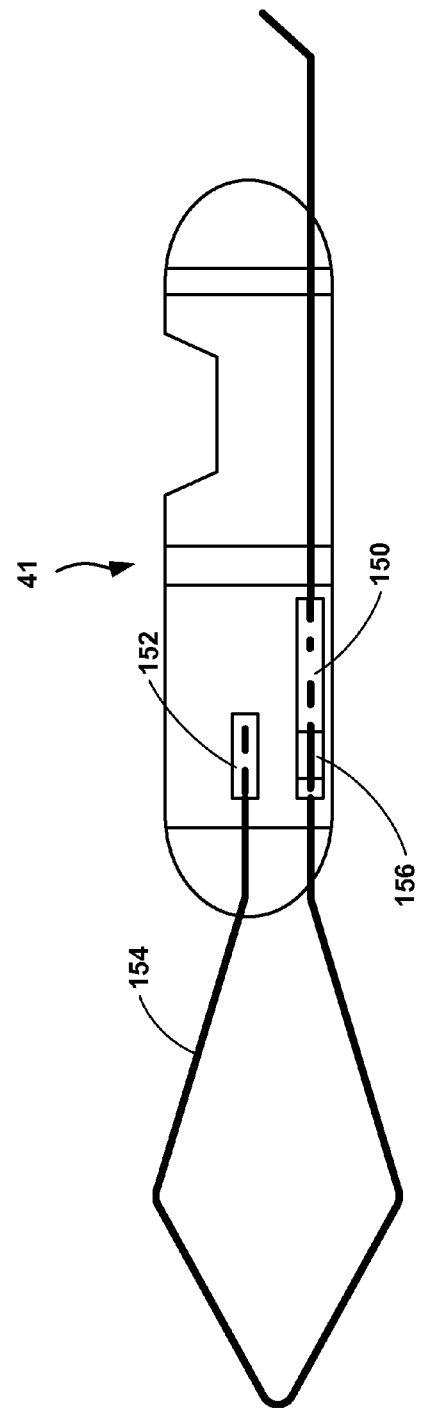

MEDICAL DEVICE FIXATION ATTACHMENT MECHANISM

This application claims the benefit of U.S. Provisional Application No. 61/408,073, entitled, "MEDICAL DEVICE FIXATION ATTACHMENT MECHANISM," and filed on Oct. 29, 2010, the entire content of which is incorporated herein by reference.

TECHNICAL FIELD

The disclosure relates to medical devices and, more particularly, fixation of medical devices.

BACKGROUND

A variety of implantable medical devices for delivering a therapy and/or monitoring a physiological condition have been clinically implanted or proposed for clinical implantation in patients. Implantable medical devices may deliver electrical stimulation or fluid therapy to, and/or monitor conditions associated with, the heart, muscle, nerve, brain, stomach or other organs or tissue, as examples. Some implantable medical devices may employ one or more elongated electrical leads carrying stimulation electrodes, sense electrodes, and/or other sensors. Implantable medical leads may be configured to allow electrodes or other sensors to be positioned at desired locations for delivery of stimulation or sensing. For example, electrodes or sensors may be carried at a distal portion of a lead. A proximal portion of the lead may be coupled to an implantable medical device housing, which may contain circuitry such as stimulation generation and/or sensing circuitry. Other implantable medical devices may be leadless and include, for example, one or more electrodes (e.g., sense and/or stimulation electrodes) on an outer surface of the medical device.

Implantable medical devices, such as cardiac pacemakers or implantable cardioverter-defibrillators, for example, provide therapeutic electrical stimulation to the heart via electrodes carried by one or more implantable leads. The electrical stimulation may include signals such as pulses or shocks for pacing, cardioversion or defibrillation. In some cases, an implantable medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm. For example, in some cases, an implantable medical device may deliver pacing pulses to the heart of the patient upon detecting tachycardia or bradycardia, and deliver cardioversion or defibrillation shocks to the heart upon detecting tachycardia or fibrillation.

SUMMARY

In general, techniques for attaching fixation members to implantable medical devices are disclosed. In one example, an implantable medical device includes a body, a fixation member, and a tube. The fixation member is configured to anchor the body to tissue of the patient. The tube is connected to the body and plastically deformed to pinch the fixation member within a hollow space of the tube.

In another example, a method includes receiving a fixation member for a medical device in a hollow space of a tube configured to be connected to the medical device and plastically deforming the tube to pinch the fixation member within the hollow space.

In another example, an attachment mechanism for a fixation member of an implantable medical device includes a tube configured to be connected to the implantable medical device and to be plastically deformed to pinch the fixation member within a hollow space of the tube.

The details of one or more examples disclosed herein are set forth in the accompanying drawings and the description below. Other features, objects, and advantages will be apparent from the description and drawings, and from the claims.

BRIEF DESCRIPTION OF DRAWINGS

FIGS. 3A and 3B are elevation and plan views, respectively, of an implantable sensor including example fixation attachment tubes.

FIGS. 5A and 5B are elevation and plan views, respectively, of an implantable sensor including another example of fixation attachment tubes according to this disclosure.

DETAILED DESCRIPTION

The following examples are directed to techniques for attaching fixation members to implantable medical devices. Implantable medical devices may be subject to various forces within the body of a patient, which may act to cause such devices to migrate from a particular implantation location and/or target tissue site for the implantable medical device. Fixation members, including, e.g., barbs, tines, stents and other such structures, may be employed to help secure (or fix or anchor) medical devices within a patient and to help prevent or inhibit migration of the device. The examples described below include methods and devices for attaching such fixation members to an implantable medical device. In particular, the disclosed examples include methods and devices for attaching a fixation member to an implantable medical device by introducing at least a portion of the fixation member into a tube mechanically connected to the medical device and plastically deforming the tube in order to pinch the fixation member within a hollow space of the tube.

Figure 1:
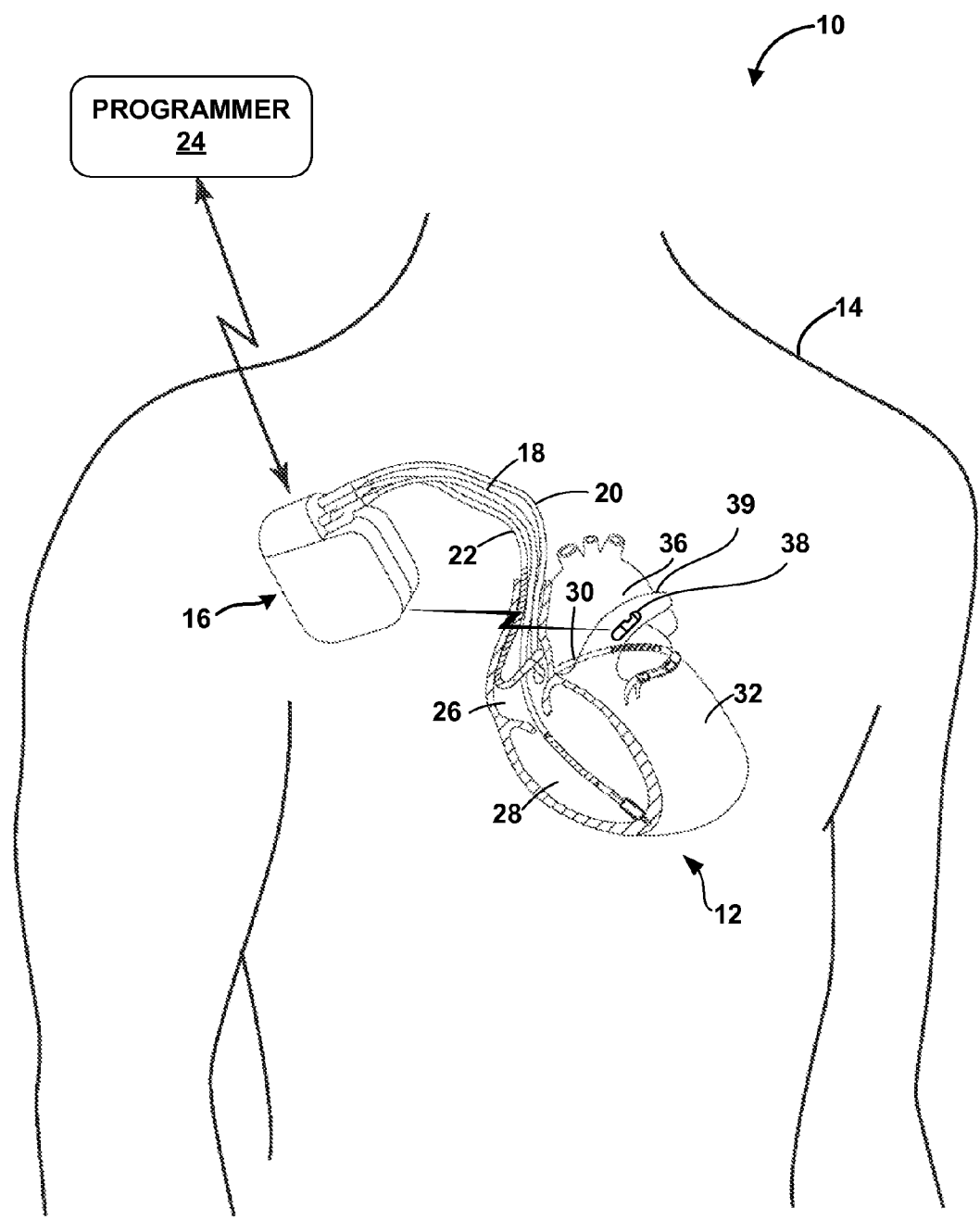
FIG. 1 is a conceptual drawing illustrating an example system that includes an implantable medical device (IMD) coupled to implantable medical leads and a leadless sensor.

FIG. 1 is a conceptual diagram illustrating an example system 10 that may be used for sensing of physiological parameters of patient 14 and/or to provide therapy to heart 12 of patient 14. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily, a human patient.

IMD 16 may include electronics and other internal components necessary or desirable for executing the functions associated with the device. In one example, IMD 16 includes one or more processors, memory, a signal generator, sensing module and telemetry modules, and a power source. In general, memory of IMD 16 may include computer-readable instructions that, when executed by a processor of the IMD, cause it to perform various functions attributed to the device herein. For example, a processor of IMD 16 may control the signal generator and sensing module according to instructions and/or data stored on memory to deliver therapy to patient 14 and perform other functions related to treating condition(s) of the patient with IMD 16.

The signal generator of IMD 16 may generate electrical stimulation that is delivered to patient 12 via electrode(s) on one or more of leads 18, 20, and 22, in order to provide, e.g., cardiac sensing, pacing signals, or cardioversion/defibrillation shocks. The sensing module of IMD 16 may monitor electrical signals from electrode(s) on leads 18, 20, and 22 of IMD 16 to in order to monitor electrical activity of heart 12. In one example, the sensing module may include a switch module to select which of the available electrodes on leads 18, 20, and 22 of IMD 16 are used to sense the heart activity. Additionally, the sensing module of IMD 16 may include multiple detection channels, each of which includes an amplifier, as well as an analog-to-digital converter for digitizing the signal received from a sensing channel for, e.g., electrogram signal processing by a processor of the IMD.

A telemetry module of IMD 16 may include any suitable hardware, firmware, software or any combination thereof for communicating with another device, such as programmer 24 (FIG. 1). Under the control of a processor of IMD 16, the telemetry module may receive downlink telemetry from and send uplink telemetry to programmer 24 with the aid of an antenna, which may be internal and/or external.

The various components of IMD 16 may be coupled to a power source, which may include a rechargeable or non-rechargeable battery. A non-rechargeable battery may be capable of holding a charge for several years, while a rechargeable battery may be inductively charged from an external device, e.g., on a daily or weekly basis.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

System 10 also includes vascular sensor 38. Sensor 38 is implanted in pulmonary artery 39. In one example, sensor 38 is configured to sense blood pressure of patient 14. For example, sensor 28 may be arranged in pulmonary artery 39 and be configured to sense the pressure of blood flowing from the right ventricle outflow tract (RVOT) from right ventricle 28 through the pulmonary valve to pulmonary artery 39. Sensor 38 may therefore directly measure the estimated pulmonary artery diastolic pressure (ePAD) of patient 14. The ePAD value is a pressure value that can be employed in patient monitoring. For example, ePAD may be used as a basis for evaluating congestive heart failure in a patient. In other examples, however, sensor 38 may be employed to measure blood pressure values other than ePAD. For example, sensor 38 may be arranged in right ventricle 28 or the pulmonary artery of heart 14 to sense RV systolic or diastolic pressure.

In some examples, sensor 38 includes a pressure sensor configured to respond to the absolute pressure inside pulmonary artery 39 of patient 14. Sensor 38 may be, in such examples, any of a number of different types of pressure sensors. One form of pressure sensor that may be useful for measuring blood pressure inside a human heart is a capacitive pressure sensor. Another example pressure sensor is an inductive sensor. In some examples, sensor 38 may also be a piezoelectric or piezoresistive pressure transducer.

Figure 2:
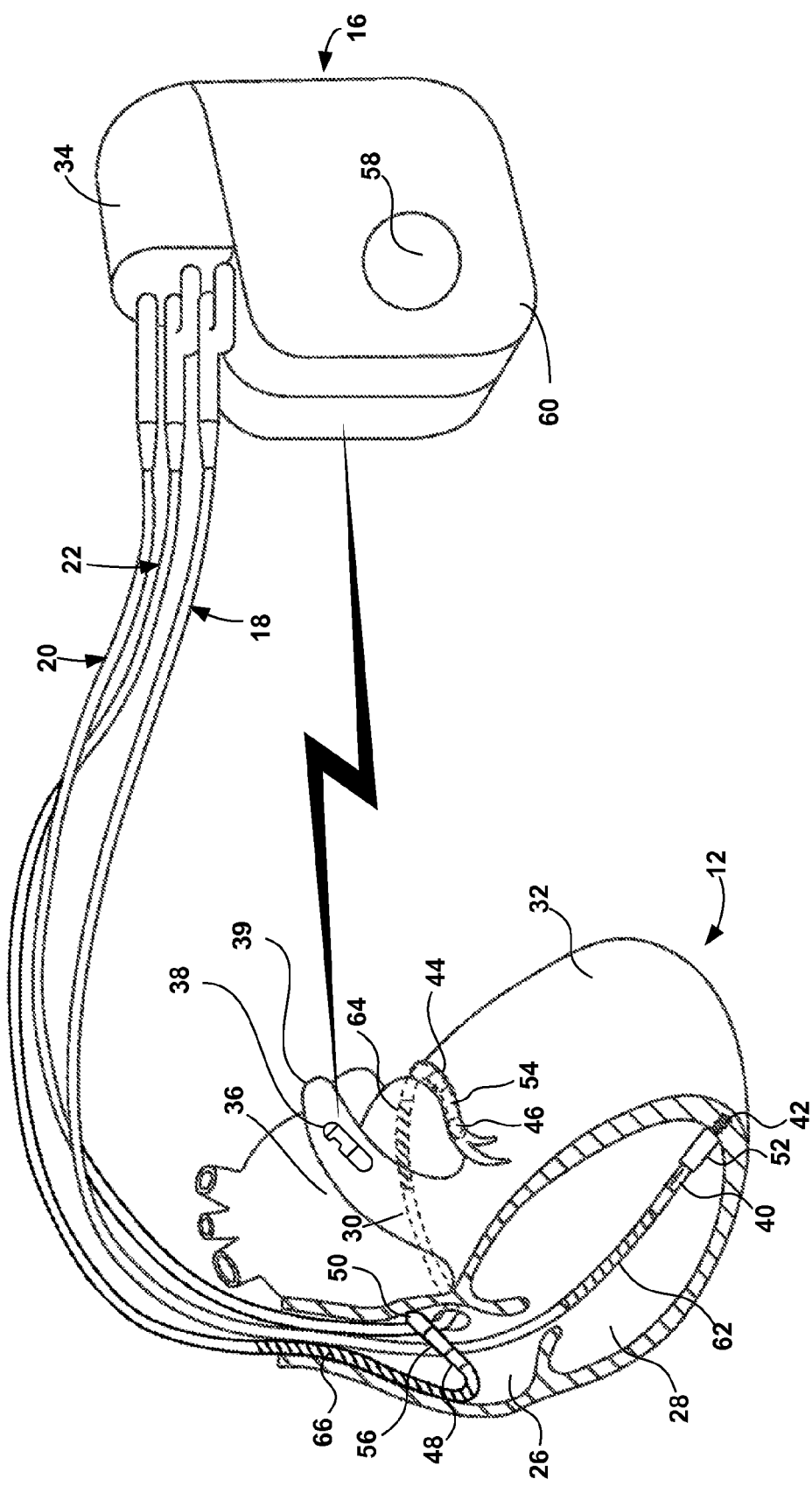
FIG. 2 is a conceptual drawing illustrating in greater detail the example IMD, leads, and sensor of FIG. 1 in conjunction with a heart.

In one example, sensor 38 is a leadless pressure sensor including capacitive pressure sensing elements configured to measure blood pressure within pulmonary artery 39. As illustrated in FIGS. 1 and 2, sensor 38 may be in wireless communication with IMD 16, e.g., in order to transmit blood pressure measurements to the IMD. Sensor 38 may employ, e.g., radio frequency (RF) or other telemetry techniques for communicating with IMD 16 and other devices, including, e.g., programmer 24. In another example, sensor 38 may include a tissue conductance communication (TCC) system by which the device employs tissue of patient 14 as a communication medium over which to send and receive information to and from IMD 16 and other devices.

As described in greater detail below with reference to FIGS. 3-7, sensor 38 may include one or more fixation members to secure the sensor within pulmonary artery 39 or to another target tissue site if sensor 38 is implanted at another location within patient 14. In one example, the one or more fixation members include a nitinol (NiTi) wire stent that is expandable to exert outward pressure on the walls of the lumen of pulmonary artery 39 to secure sensor 38 within the vessel. The examples described below include methods, systems, and devices for attaching such fixation members to sensor 38, or other implantable medical devices. In particular, the disclosed examples include methods, systems, and devices for attaching the fixation member to sensor 38 by introducing at least a portion of the fixation member into a tube mechanically connected to the medical device and plastically deforming the tube connected to the sensor in order to pinch the fixation member within a hollow space of the tube.

Referring again to FIG. 1, system 10 may, in some examples, additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, therapy system 10 may include temporary or permanent epicardial or subcutaneous leads, instead of or in addition to leads 18, 20 and 22. Such leads may be used for one or more of cardiac sensing, pacing, or cardioversion/defibrillation.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 detects fibrillation employing any of a number of known fibrillation detection techniques.

Programmer 24 shown in FIG. 1 may be a handheld computing device, computer workstation, or networked computing device. Programmer 24 may include electronics and other internal components necessary or desirable for executing the functions associated with the device. In one example, programmer 24 includes one or more processors and memory, as well as a user interface, telemetry module, and power source. In general, memory of programmer 24 may include computer-readable instructions that, when executed by a processor of the programmer, cause it to perform various functions attributed to the device herein. Memory, processor(s), telemetry, and power sources of programmer 24 may include similar types of components and capabilities described above with reference to similar components of IMD 16.

In one example, programmer 24 includes a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, and 22, or a power source of IMD 16. In some examples, this information may be presented to the user as an alert.

The user may use programmer 24 to program a therapy progression, select electrodes used to deliver electrical stimulation to heart 12 (e.g., in the form of pacing pulses or cardioversion or defibrillation shocks), select waveforms for the electrical stimulation, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication, e.g. via telemetry modules in each of the devices using any number of known techniques. Examples of communication techniques may include, for example, low frequency or RF telemetry, but other techniques are also contemplated. In some examples, programmer 24 may include a programming head that may be placed proximate to the patient's body near the IMD 16 implant site in order to improve the quality or security of communication between IMD 16 and programmer 24.

FIG. 2 is a conceptual diagram illustrating IMD 16 and leads 18, 20 and 22 of therapy system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Other lead configurations may also be used. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other embodiments, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The sensed electrical signals may be processed as the EMG signal by IMD 16.

Any combination of electrodes 40, 42, 44, 46, 48, 50, 58, 62, 64 and 66 may be considered a sensing configuration that has one or more electrodes. In some examples, a sensing configuration may be a bipolar electrode combination on the same lead, such as electrodes 40 and 42 of lead 18. In any sensing configuration, the polarity of each electrode in the sensing configuration may be configured as appropriate for the application of the sensing configuration.

In some examples, IMD 16 delivers pacing pulses via bipolar combinations of electrodes 40, 42, 44, 46, 48 and 50 to cause depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver cardioversion or defibrillation pulses to heart 12 via any combination of elongated electrodes 62, 64, 66, and housing electrode 58. Electrodes 58, 62, 64, 66 may also be used to deliver cardioversion pulses, e.g., a responsive therapeutic shock, to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26.

FIGS. 3A and 3B are elevation and plan views, respectively, of sensor 38 including example fixation attachment tubes 100 connecting stent 102 to the sensor. Sensor 38 also includes battery 104, sensing elements 106, TCC electrodes 108, and sensor placement loop 110. In the example of FIGS. 3A and 3B, sensing elements 106 and other electronic components of sensor 38, e.g., a TCC system, is powered by battery 104. Sensing elements 106 may include any suitable sensing elements for sensing a physiological parameter of patient 14, such as, but not limited to capacitive sensing elements to measure internal pressures within patient 14, including, e.g. blood pressure within pulmonary artery 39. In one example, battery 104, sensing elements 106, and other internal components of sensor 38 may be substantially fully encapsulated within an external housing, which may be, e.g., hermetically sealed to inhibit contact of body fluids with the components of the sensor and migration of chemicals within the sensor to the body of patient 14.

Sensor 38 may, in one example, communicate with, e.g., IMD 16 and programmer 24 with a TCC system via TCC electrodes 108 arranged at opposite ends of the sensor. The TCC system of sensor 38 may employ tissue of patient 14 as a communication medium over which information can be sent to and received from IMD 16 and other devices. In another example, sensor 38 may employ, e.g., RF or other telemetry techniques for communicating with IMD 16 and other devices, including, e.g., programmer 24.

Sensor 38 includes stent 102, which is configured to expand to push against tissue of patient 14 to help secure the sensor within the patient and help inhibit migration of the device over time. For example, sensor 38 may be implanted within pulmonary artery 39 of patient 14, in which stent 102 may push against the walls of the lumen of the artery to secure the sensor at an implantation location. Stent 102 is illustrated in FIG. 3A in an expanded state. However, prior to placement of sensor 38 within patient 14, legs 102a of stent 102 may be held in a collapsed state, e.g., by a sheath over the stent within a delivery catheter employed to implant the device or by an inner surface of a lumen of the delivery catheter. Once the implanting clinician delivers sensor 38 to the target location within patient 14, the sheath surrounding and collapsing stent 102 may be retracted to permit the stent to expand and push against surrounding tissue of the patient. In one example, stent 102 may be a resilient nitinol (NiTi) wire fixation member. In other examples, stent 102 may be fabricated from other materials, including, e.g., other biocompatible metallic alloys, plastics, or other materials suitable for use in conjunction with sensor 38. Other suitable techniques can be used to restrain stent 102, e.g., to minimize the overall dimension of sensor 38 and stent 102 in a direction substantially perpendicular to an axis that extends between TCC electrodes 108 as sensor 38 and stent 102 are being implanted in patient 14.

In the example of FIGS. 3A and 3B, sensor 38 also includes sensor placement loop 110. Sensor placement loop 110 may be employed by the implanting clinician, or another clinician, to place, manipulate, retract, reposition sensor 38 during implantation. For example, after placing sensor 38 within patient 14 and retracting a sheath surrounding stent 102, the implanting clinician may wish or need to reposition the sensor. The clinician may, in such circumstances, employ placement loop 110 to retract sensor 38 such that stent 102 is pulled back into and collapsed by the sheath, which, in turn, permits the clinician to reposition the sensor within patient 14. Placement loop 110 and stent 102 may be fabricated as separate components, from different materials, and connected to sensor 38 via attachment tubes 100. In another example, however, placement loop 110 and stent 102 may be fabricated from the same materials and may be mechanically coupled to one another, e.g. within attachment tubes 100.

Figure 4A:
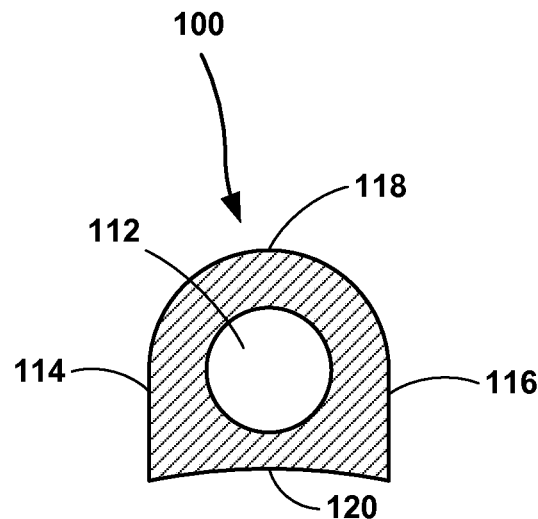
FIGS. 4A and 4B section views of one of the fixation attachment tubes of FIGS. 3A and 3B cut along section line A-A in FIG. 3A.
Figure 4B:
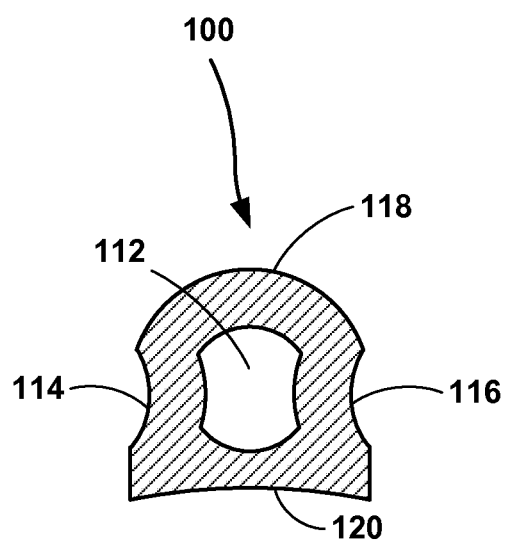

Stent 102, as well as placement loop 110, are mechanically connected to sensor 38 by fixation attachment tubes 100, which are mechanically connected to the outer surface of sensor 38. In the example of FIGS. 3A and 3B, fixation attachment tubes 100 each include an elongated member that defines an aperture running through the tubes from one end to the other. That is, the aperture defined by the elongated member may include an opening at respective ends of the elongated member. In some examples, a tube refers to a structure defined by one or more walls that substantially surround and define an aperture through into which a portion of a fixation member for an implantable medical device may be received. The walls of such tubes may be plastically deformed to pinch the portion of the fixation member disposed within the aperture of the tube. In the example of FIGS. 3A and 3B, attachment tubes 100 are approximately one third as long as sensor 38. However, in other examples tubes 100 may be longer or shorter relative to sensor 38. FIGS. 4A and 4B are sectional views of one of attachment tubes 100 cut along section line A-A in FIG. 3A and illustrate an example in which a portion of stent 102 is pinched by tube 100.

FIGS. 4A and 4B illustrate attachment tube 100 before and after, respectively, the tube has been plastically deformed to pinch a portion of stent 102 disposed within aperture 112 of the tube. In the example of FIGS. 4A and 4B, attachment tube 100 includes two substantially linear walls 114, 116, e.g., side walls in the view shown, and two curvilinear walls 118, 120, e.g., top and base, respectively, in the view shown. In one example, attachment tube 100 may include aperture 112 approximately 0.41 millimeters (0.016 inches) across, e.g. in diameter, with one or more of walls 114-120 with a thickness in a range from approximately 0.1 millimeters (0.004 inches) to approximately 0.25 millimeters (0.010 inches). Stent 102 may, in one example, have a cross-section, e.g. square or round, in a range from approximately 0.2 millimeters (0.008 inches) to approximately 0.31 millimeters (0.012 inches) across. Aperture 112 extends from one end of attachment tube 100 to the other. Aperture 112 is generally centrally aligned with rounded top 118 of tube 100, such that a center of aperture 112 is generally aligned with a center of rounded top 118. However, in other examples, aperture 112 may be arranged eccentric with top 118 or more generally with the whole of tube 100. Base 120 of tube 100 is contoured to define a surface (e.g., a curvilinear surface in the example shown in FIGS. 4A and 4B) that mates with the rounded outer surface of sensor 38. In other examples, tube 100 may include a side that is contoured in a different manner to mate with an outer surface of an implantable device with a different shape than sensor 38. Additionally, in other examples, tube 100 may include a cylindrical tube, including, e.g., a curvilinear or a rectilinear cylinder. For example, tube 100 may include one of circular, elliptical, square, or rectangular cylinder.

Aperture 112 of attachment tube 100 is configured to receive a portion of stent 102, and, in the example of FIGS. 3A and 3B, sensor placement loop 110. In some examples, aperture 112, stent 102, and sensor placement loop 110 have substantially similar cross-sectional shapes or at least cross-sectional shapes and sizes that are compatible and permit stent 102 and sensor placement loop 110 to be introduced into aperture 112. For example, aperture 112 can be generally circular in cross-section (as shown in FIG. 4A) such that it is configured to receive an end of stent 102, which may be a wire (e.g., nitinol wire), cut from sheet and heat set or cut from tube and heat set. In other examples, tube 100 and aperture 112 may include other shapes, examples of which will be described below with reference to FIGS. 7A-7E.

After receiving an end of stent 102, sides 114, 116 of tube 100 may be plastically deformed, e.g., as illustrated in FIG. 4B, to pinch the stent within aperture 112. Pinching stent 102 describes the process by which the walls of tube 100, sides 114, 116 collapse onto the outer surface of the stent to exert a compressive force on the stent that holds it within aperture 112 of the tube. The compressive force of sides 114, 116 of tube 100 on stent 102 is maintained because the tube has been irreversibly, i.e. plastically deformed such that the sides of the tube stay in the collapsed state shown in FIG. 4B even after the compressive force that causes the deformation of the sides of the tube is removed. In this manner, stent 102 is attached to sensor 38 via tubes 100 without the advent of any additional components or processes, including, e.g. without using an adhesive or epoxy. Additionally, in one example, wall 118 may also be collapsed to apply additional compressive force on stent 102. This process may be repeated for stent 102 and any of tubes 100 in FIGS. 3A and 3B. In some examples, stent 102 may be used to facilitate wireless communications to and from sensor 38, e.g. the stent may form part of an antenna of the sensor, e.g. along with TCC electrodes 108. In such an example, crimping stent 102 within aperture 112 of attachment tubes 100 may also function to establish an electrical connection between the stent and TCC electrodes 108. The same process may be employed to attach sensor placement loop 110 to sensor 38 by plastically deforming tubes 100 to pinch the placement loop within aperture 112. Any compressive tool may be employed to deform tube 100 to pinch a portion of stent 102 and/or loop 110 within aperture 112. For example, a crimping tool including a pair of jaws configured to press sides 114, 116 inward toward aperture 112 may be employed to deform attachment tube 100.

In one example, approximately 2.3 millimeters (0.090 inches) of stent 102 may be inserted into attachment tube 100 and the length of the attachment tube that is crimped, i.e. plastically deformed to pinch the stent within aperture 112 may be approximately 0.76 millimeters (0.030 inches). Additionally, the crimped portion of attachment tube 100 may be, e.g., approximately centered along the length of the tube such that there is sufficient undeformed material of the attachment tube on either side of the crimped portion. To assist in placing stent 102 in aperture 112 of attachment tube 100, in one example, the stent may include a marking that indicates how far to push the stent into the tube. Additionally or alternatively, an opening on attachment tube 100 may assist in the placement of stent 102 by allowing the end of the stent to be seen after being introduced a known distance into the tube, the distance defined by the location of the opening. Such an opening in one of attachment tubes 100 may also assist with cleaning the tube.

Attachment tubes 100 are constructed of a material that permits the tubes to be plastically deformed upon the application of force to walls 114, 116 of tubes 100. Attachment tubes 100 illustrated in FIGS. 3A-4B may be formed from a variety of types of materials including, e.g., titanium and other biocompatible metals, e.g. other metals or biocompatible plastics. In one example, attachment tubes 100 are formed from an American Society for Testing and Materials (ASTM) grade titanium in a range from grade 1 to 5, the standards for which are set by ASTM International of West Conshohocken, Pa. In some examples, attachment tubes 100 constructed from softer materials may perform better than those constructed from harder materials. For example, attachment tubes 100 constructed from ASTM titanium grades 1-3 may perform better than grades 4 and 5. In one example, attachment tubes 100 include an ATSM grade titanium in a range from grade 1 to 4. In another example, attachment tubes 100 include an ATSM grade titanium in a range from grade 1 to 2. ASTM titanium grades 1-4 are all unalloyed ("pure") forms of titanium. ASTM titanium grade 5 is an alloy comprising 5.5-6.75% by weight of aluminum (Al), 3.5-4.5% by weight of vanadium (V), a maximum of 0.2% by weight of $O_2$, 0.4% by weight of iron (Fe), 0.015% by weight of $H_2$, 0.10% by weight of carbon (C), and 0.05% by weight of $N_2$. ASTM titanium grade 23, or Ti-6Al-4V, extra low interstitial (ELI) is an alloy comprising 5.5-6.75% by weight of aluminum (Al), 3.5-4.5% by weight of vanadium (V), a maximum of 0.13% by weight of $O_2$, 0.25% by weight of iron (Fe), 0.01525% by weight of $H_2$, 0.08% by weight of carbon (C), and 0.05% by weight of $N_2$. Some of the properties of ASTM grade titanium, grades 1-5 are summarized below in Table 1.

TABLE 1

| ASTM Grade | Alloy Composition | Min. Tensile (KSI/MPa) | Min. Yield (KSI/MPa) | Modulus of Elasticity (PSI × $10^6$/ GPa) |
|---|---|---|---|---|
| 1 | Unalloyed Ti 35A | 35/241 | 25/172 | 14.9/103 |
| 2 | Unalloyed Ti 50A | 50/345 | 40/276 | 14.9/103 |

TABLE 1-continued

| ASTM Grade | Alloy Composition | Min. Tensile (KSI/MPa) | Min. Yield (KSI/MPa) | Modulus of Elasticity (PSI × $10^6$/ GPa) |
|---|---|---|---|---|
| 3 | Unalloyed Ti 65A | 65/448 | 55/379 | 14.9/103 |
| 4 | Unalloyed Ti 80A | 80/552 | 70/483 | 15/103 |
| 5 | Ti—6Al—4V | 130/896 | 120/827 | 16.4/113 |
| 23 | Ti—6Al—4V, ELI | 120/828 | 110/759 | 16.3/112 |

Unalloyed titanium grades are often referred to by their tensile strengths, including, e.g., 35A for grade 1, 50A for grade 2, 65A for grade 3, 80A for grade 4. The difference between different unalloyed titanium grades includes the sub-percentage traces of oxygen and iron in the metal. The more of these dopants (inclusions, contaminants) present in the particular grade, the harder the metal becomes.

Referring again to FIGS. 3A and 3B, attachment tubes 100 are connected to an outer surface of sensor 38. In the example shown in FIGS. 3A and 3B, tubes 100 are connected to an outer surface of the housing of sensor 38 surrounding battery 104 toward one end of the sensor 38 (e.g., closer to one end of sensor 38 than an opposite end of the sensor). In another example, tubes 100 may be connected toward the other end of sensor 38. Connecting attachment tubes 100 to the side of sensor 38 toward, but not at the end of the sensor, i.e., one of the ends including TCC electrodes 108, cantilevers the sensor such that it may act to reduce the moment arm from the point at which stent 102 anchors sensor 38 to tissue of patient 14 to the connection between attachment tubes 100 and the sensor, which, in turn, may act to reduce stresses on the tubes and the sensor. Connecting attachment tubes 100 to sensor 38 in the manner illustrated also transfers loads from stent 102 to the body of the sensor, thereby protecting TCC electrodes 108 at the ends of the sensor. In examples in which sensor 38, e.g. sensing elements 106 are configured to sense pressure, cantilevering the sensor from tubes 100 may also reduce the impact of strain loads on the output of the sensing elements. Additionally, attaching tubes 100 to battery 104, versus sensing elements 106 may help reduce the potential to cause offset and drift to sensor output and the impact of strain loads.

A variety of techniques may be employed to mechanically connect attachment tubes 100 to sensor 38, including, e.g., welding (e.g., with any suitable source of energy, such as a gas flame, an electric arc, a laser, an electron beam, friction, and ultrasound) or adhering the attachment tubes to the sensor. For example, an adhesive or epoxy may be employed to adhere attachment tubes 100 to sensor 38. In one example, attachment tubes 100 and an outer housing of sensor 38 may be fabricated from titanium alloy(s), in which case, welding the tubes to the sensor may be appropriate. Other appropriate methods for connecting attachment tubes 100 to sensor 38 are contemplated. For example, a case enclosing battery 104 of sensor 38 may be fabricated, e.g. cast or machined, with attachment tubes 100 integral with the case.

FIGS. 5A and 5B are elevation and plan views, respectively, of example sensor 41 including example fixation attachment tubes 150, 152 mechanically connecting stent 154 to the sensor. The constituent components of sensor 41, other than attachment tubes 150 and stent 154, may be similar in constitution and arrangement as sensor 38 described above with reference to the example of FIGS. 3A and 3B. However, in the example of FIGS. 5A and 5B, the configuration of stent 152 necessitates the alternative configuration of attachment tubes 150, which are notched to provide accessibility for a tool to plastically deform attachment tubes 152.

In FIGS. 5A and 5B, stent 154 is connected to sensor 41 by fixation attachment tubes 150 and 152, which are connected to the outer surface of sensor 41, e.g., using a mechanical attachment technique similar to that used to mechanically connect tube 100 to sensor 38 (FIGS. 3A and 3B). Fixation attachment tubes 150 and 152 each include an elongated member that defines an aperture running through the tubes from one end to the other. As with attachment tubes 100, the aperture of each tubes 150 and 152 is configured to receive a portion of stent 154 and the tubes are configured to be plastically deformed to pinch the stent within the aperture. Unlike the example of FIGS. 3A and 3B, stent 154 includes two elements connected to sensor 41 via attachment tubes 150 and 152 at four different locations. The configuration of stent 154 necessitates two pairs of two attachment tubes, each of which pair includes one tube 150 and one tube 152. In this arrangement, depending on the proximity of tubes 150, 152 to an adjacent tube, it may be difficult to access tubes 152 with a tool to deform the tube due to interference from tubes 150, each of which is arranged adjacent each tube 152. As such, tubes 150 include notches 156, which provide clearance between tubes 150, 152 for a tool, e.g., one jaw of a crimping tool, to access tubes 152, e.g., in order to plastically deform the tubes to pinch the ends of stent 154 within the aperture of the tubes.

In other examples, a fixation member may be attached to a medical device with fewer or more attachment tubes than illustrated in the examples of FIGS. 3A and 3B, and 5A and 5B. For example, a fixation member may be attached to a medical device with one or three fixation attachment tubes. In other examples, a medical device may include multiple fixation members, each of which may be attached to the device with one or more attachment tubes. Additionally, in one example, multiple fixation members may be introduced into one tube (or another such mechanism), e.g. at either end of the tube similar to the configuration of stent 102 and placement loop 110 in the example of FIGS. 3A and 3B, that may then be deformed to pinch the fixation members within the tube and, thereby, connect them to a medical device. Multiple fixation members may also be introduced through the same end of one of attachment tubes 100 and pinched in place. In one example including one fixation member connected to sensor 38 with one attachment tube 100, the attachment tube may be plastically deformed in multiple locations to increase the compressive force applied on the fixation member to more securely mechanically connect it to the sensor. In addition, although the fixation attachment mechanism is described herein as a tubular structure, this term or configuration should not be interpreted as limiting. For example, fixation members may be attached to a medical device via any mechanism that is capable of receiving a portion of the fixation member and being plastically deformed to connect the fixation member to the attachment mechanism.

Figure 6:
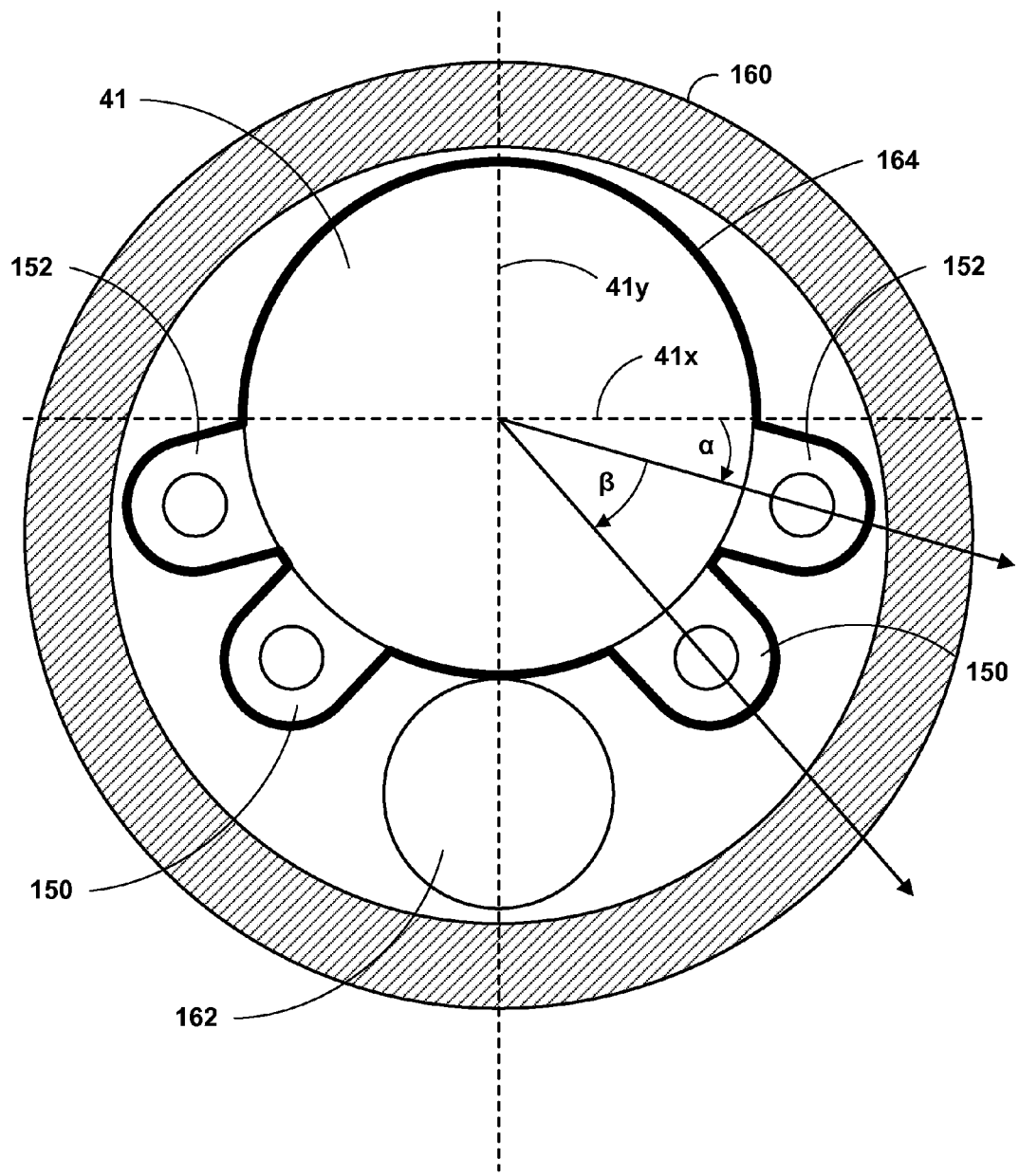
FIG. 6 is a conceptual partial sectional drawing illustrating a sensor and attachment tubes arranged within a delivery catheter.

FIG. 6 is a conceptual partial sectional drawing illustrating of sensor 41 and attachment tubes 150 and 152 arranged within delivery catheter 160, which may be used, e.g., to implant the sensor within the body of patient 14. Stent 154 is omitted from FIG. 6 to more clearly illustrate the placement of attachment tubes 150 and 152 relative to sensor 41. Delivery catheter 160 may be employed as part of, e.g., an endoscopic implantation system for guiding sensor 41 to and implanting the sensor at an implantation location within patient 14, e.g. in pulmonary artery 39. In one example, delivery catheter 160 is directed through a vein into right atrium 26, then right ventricle 28 and through the right ventricle outflow tract (RVOT) from the right ventricle 28 through the pulmonary valve to pulmonary artery 39. Sensor 41 and guide wire 162 are received within and carried by delivery catheter 160. Guide wire 162 may be employed to stabilize and guide the placement sensor 41 at a desired location within patient 14, including, e.g., within pulmonary artery 39. In one example, catheter 160 may include a guide wire lumen in which guide wire 162 may be arranged. In such an example, guide wire 162 may be placed at a target site within patient 14 first and sensor 41 may be guided along the guide wire to the site of implant.

The example of FIG. 6 illustrates the placement of fixation attachment tubes 150 and 152 on the outer surface of sensor 41. FIG. 6 includes axis lines 41x and 41y, which are perpendicular to one another and intersect at the center of the cross-section of sensor 41. Attachment tubes 150 and 152 can be arranged circumferentially on the outer surface of sensor 41 so as to reduce or minimize the overall size of the delivery system, e.g. catheter 160 that delivers the sensor with attachment tubes to an implant site. In the example of FIG. 6, attachment tubes 150 are arranged at an angle α below axis line 41x and attachment tubes 152 are arranged at an angle β below axis line 41x. By not aligning any of attachment tubes 150 and 152 with either of axis lines 41x, 41y, the size of delivery catheter 160 is improved, i.e. reduced relative to aligning the tubes with the axis lines, which, in turn, may improve the maneuverability of the catheter within vessels of patient 14.

In some examples, introducing sensor 41 with attachment tubes 150 plastically deformed into a patient's body may cause one or more side effects. For example, plastically deforming attachment tubes 150 may deform the outer surfaces of the tubes, which, in turn, may lead to thrombus formation. In order to reduce the risk of thrombus formation, or other side effects caused by the character of the outer surfaces of attachment tubes 150 and sensor 41, in one example, the sensor may be encased in sheath 164 illustrated in FIG. 6. Sheath 164 may be fabricated from a number of biologically inert materials, including, e.g. silicone. In one example, a medical adhesive may be backfilled between sheath 164 and the outer surfaces of sensor 41 and attachment tubes 150 to secure the sheath to the sensor and tubes.

Figure 7A:
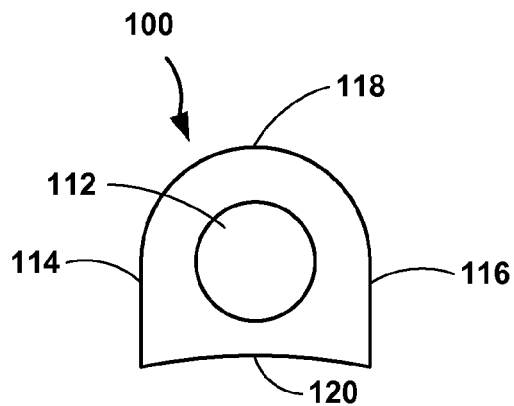
FIGS. 7A-7E illustrate example shapes into which attachment tubes in accordance with this disclosure may be formed.
Figure 7B:
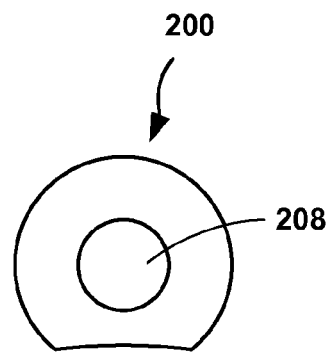
Figure 7C:
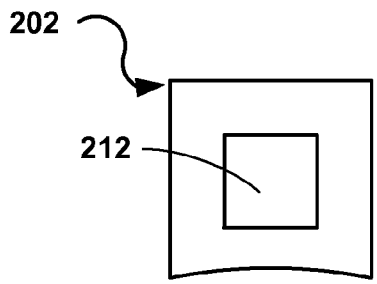
Figure 7D:
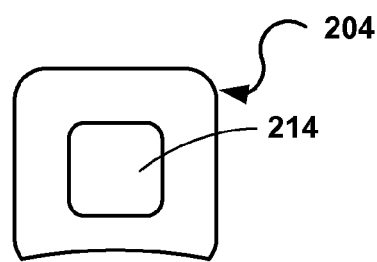
Figure 7E:
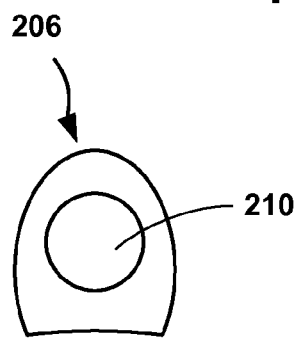

FIGS. 7A-7E illustrate a number example shapes into which attachment tubes in accordance with this disclosure may be formed. FIGS. 7A-7E illustrate schematic cross-sectional views of the attachment tubes, where the cross-section is taken in a direction substantially perpendicular to an axis that extends between ends of the aperture configured to receive the fixation member. FIG. 7A illustrates attachment tube 100 shown and described with reference to FIGS. 3A-4B. Attachment tube 100 includes a combination of generally straight and curved sides, including straight sides 114, 116 and curved top 118, and base 120. The rest of the example attachment tubes 200, 202, 204, 206 illustrated in FIGS. 7B, 7C, 7D, 7E, respectively, include cylindrical tubes cut to form a contoured surface that may be configured to, e.g., mate with an outer surface of a medical device to which the tubes may be connected. FIG. 7B includes generally circular cylindrical tube 200. FIGS. 7C and 7D include generally rectangular cylindrical tubes 202 and 204, respectively. The example tubes 202, 204 of FIGS. 7C, 7D, respectively, are generally shaped with equal length sides to form generally square profiles. However, in other examples, a rectangular cylindrical tube may be formed with two pairs of two sides of differing length. FIG. 7E includes elliptical cylindrical tube 206.

The examples of FIGS. 7A-7E also illustrate that the aperture in attachment tubes according to this disclosure may be formed into different shapes. For example, apertures 112, 208, and 210 of tubes 100, 200, and 206, respectively, are generally circular. However, apertures 212 and 214 of tubes 202 and 204, respectively, are generally rectangular. As discussed above, apertures of attachment tubes can be configured (e.g., sized and shaped) to receive and engage with a fixation member.

Figure 8:
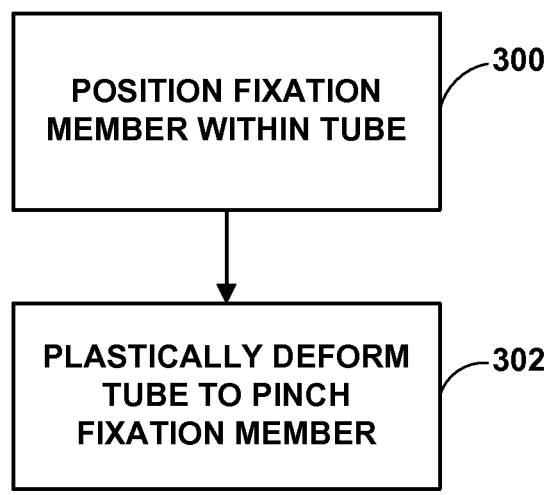
FIG. 8 is a flow chart illustrating an example method of attaching a fixation member to a medical device.

FIG. 8 is a flow chart illustrating an example method of attaching a fixation member to an IMD. The method of FIG. 8 includes positioning a fixation member for a medical device in a hollow space defined by a tube configured to be mechanically connected to the medical device (300) and plastically deforming the tube to pinch the fixation member within the hollow space (310). The functions of the method of FIG. 8 are described with reference to example sensor 38, attachment tubes 100, and stent 102 of FIGS. 3A and 3B. However, in other examples, the method of FIG. 8 may be applied to other implantable medical devices employing differently configured fixation attachment mechanisms. For example, the techniques included in the example method of FIG. 5 may be applied to attaching stent 154 to example sensor 41 of FIGS. 5A and 5B with attachment tubes 150 and 152.

In one example, the method of FIG. 8 includes positioning a fixation member for a medical device in a hollow space defined by a tube configured to be mechanically connected to the medical device (300). For example, an end of stent 102 may be positioned within aperture 112 of attachment tube 100 as illustrated in FIGS. 3A and 3B.

The method of FIG. 8 also includes plastically deforming the tube to pinch the fixation member within the hollow space (310). After positioning an end of stent 102 in aperture 112 of tube 100, sides 114, 116 of tube 100 may be plastically deformed, e.g., as illustrated in FIG. 4B, to pinch the stent within aperture 112. This process may be repeated for all of the attachment locations between any of tubes 100 in FIGS. 3A and 3B and stent 102 and sensor placement loop 110. Any compressive tool may be employed to deform tube 100 to pinch a portion of stent 102 and/or loop 110 within aperture 112. For example, a crimping tool including a pair of jaws configured to press sides 114, 116 inward toward aperture 112 may be employed to deform attachment tube 100.

The process of positioning stent 102 within aperture 112 of tubes 100 and deforming the tubes to pinch the stent may be partially or completely manually executed by an operator, e.g., employing a hand crimping tool. In another example, however, automated machinery may index and position attachment tubes 100 and stent 102 with respect to one another, and automatically deform the tubes to pinch the stent in aperture 112.

In one example, the method of FIG. 8 may also include mechanically connecting the tube to the IMD. For example, tube 100 may be mechanically connected to sensor 38. A variety of techniques may be employed to mechanically connect attachment tubes 100 to sensor 38, including, e.g., welding (e.g., with any suitable source of energy, such as a gas flame, an electric arc, a laser, an electron beam, friction, and ultrasound) or adhering the attachment tubes to the sensor. For example, an adhesive or epoxy may be employed to adhere attachment tubes 100 to sensor 38. In one example, attachment tubes 100 and an outer housing of sensor 38 may be fabricated from titanium alloy(s), in which case, welding the tubes to the sensor may be appropriate. Other appropriate methods for connecting attachment tubes 100 to sensor 38 are contemplated.

Although fixation attachment techniques according to this disclosure are described in the context of cardiac devices, and, in particular, sensors for cardiac systems, the examples disclosed herein may also be employed to place other types of implantable medical devices. In some examples, a fixation attachment mechanism in accordance with this disclosure may be employed with medical devices that deliver therapy via a medical lead. For example, a fixation attachment mechanism in accordance with the disclosed examples may be employed in a neurostimulation system for spinal cord, gastric, pelvic floor, or deep brain stimulation delivered via one or more electrical stimulation leads. In another example, the examples disclosed herein may be used in conjunction with implantable fluid delivery systems, e.g., implantable drug pumps that are configured to deliver therapeutic fluids via a catheter. A fixation attachment mechanism in accordance with this disclosure may also be employed with an implantable microstimulator.

In addition, therapy system 10 is not limited to treatment of a human patient. In alternative examples, therapy system 10 may be implemented in non-human patients, e.g., primates, canines, equines, pigs, and felines. These other animals may undergo clinical or research therapies that may benefit from the subject matter of this disclosure.

Some techniques described in this disclosure, including those attributed to IMD 16, programmer 24, sensor 38, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" as used herein may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure. The term "memory" as used herein may generally refer to any of the foregoing types of computer-readable storage media, alone or in combination with other logic circuitry, or any other equivalent circuitry. The computer-readable storage medium may be nontransitory.

Various examples have been described. These and other examples are within the scope of the following claims.

The invention claimed is:

1. An implantable medical device comprising:
a body configured to house at least one internal component, wherein the internal component comprises a sensing element configured to sense a physiological parameter of a patient and wherein the sensing element comprises at least one of a temperature, pressure, or perfusion sensor;
a fixation member configured to anchor the body to tissue of the patient; and
a tube connected to the body and plastically deformed to pinch the fixation member within a hollow space defined by the tube.

2. The device of claim 1, wherein the fixation member comprises flexible wire configured to be formed into one or more shapes adapted to engage tissue of the patient to anchor the body to the tissue.

3. The device of claim 2, wherein the fixation member comprises a nickel titanium (NiTi) alloy.

4. The device of claim 1, wherein the tube comprises titanium (Ti).

5. The device of claim 4, wherein the titanium comprises an American Society for Testing and Materials (ASTM) grade titanium in a range from 1 to 5.

6. The device of claim 5, wherein the titanium comprises an ASTM grade titanium in a range from grade 1 to 4.

7. The device of claim 6, wherein the titanium comprises an ASTM grade titanium in a range from grade 1 to 2.

8. The device of claim 4, wherein the titanium comprises an American Society for Testing and Materials (ASTM) grade 23 titanium.

9. The device of claim 1, wherein the tube is connected to the body by at least one of a weld or an adhesive.

10. The device of claim 1, wherein the tube comprises a cylindrical tube.

11. The device of claim 1, wherein the tube comprises a curvilinear cross-section or a rectilinear cross-section.

12. The device of claim 11, wherein the tube comprises at least one of a circular cross-section, an elliptical cross-section, or a rectangular cross-section.

13. The device of claim 1, wherein the body comprises a cylindrical shape and an outer surface of the tube is contoured to mate with an outer surface of the substantially cylindrical body.

14. An implantable medical device comprising:
a body configured to house at least one internal component, wherein the internal component comprises a sensing element configured to sense a physiological parameter of a patient and wherein the body is configured to house a battery configured to power at least the sensing element and arranged toward an end of the body opposite the sensing element;
a fixation member configured to anchor the body to tissue of the patient; and
a tube connected to the body and plastically deformed to pinch the fixation member within a hollow space defined by the tube, wherein the tube is connected to the end of the body toward which the battery is arranged.

15. An implantable medical device comprising:
a body configured to house at least one internal component;
a fixation member configured to anchor the body to tissue of the patient; and
a tube connected to the body and plastically deformed to pinch the fixation member within a hollow space defined by the tube, wherein the tube is connected to a side of the body closer to one end of the body than another end of the body.

16. An implantable medical device comprising:
a body configured to house at least one internal component;
a fixation member configured to anchor the body to tissue of the patient;
a tube connected to the body and plastically deformed to pinch the fixation member within a hollow space defined by the tube; and
one or more additional tubes, wherein the tube and the one or more additional tubes are each plastically deformed to pinch a portion of the fixation member.

17. The device of claim 16, wherein the tube and the one or more additional tubes comprises two tubes, each of which is connected to a side of the body closer to one end of the body than another end of the body.

18. The device of claim 17, wherein at least one of the two tubes comprises a notch.

19. An implantable medical device comprising:
a body configured to house at least one internal component;
a fixation member configured to anchor the body to tissue of the patient; and
a tube connected to the body and plastically deformed to pinch the fixation member within a hollow space defined by the tube, wherein the tube is connected to a side of the body.

* * * * *